US012685699B2

(12) United States Patent
Inaka

(10) Patent No.: US 12,685,699 B2
(45) Date of Patent: Jul. 21, 2026

(54) OIL-BASED LIQUID COSMETIC

(71) Applicant: JO COSMETICS CO., LTD., Toyko (JP)

(72) Inventor: Takuma Inaka, Tokyo (JP)

(73) Assignee: JO COSMETICS CO., LTD., Tokyo (JP)

( * ) Notice: Subject to any disclaimer, the term of this patent is extended or adjusted under 35 U.S.C. 154(b) by 276 days.

(21) Appl. No.: 18/288,844

(22) PCT Filed: Mar. 24, 2022

(86) PCT No.: PCT/JP2022/013806
§ 371 (c)(1),
(2) Date: Oct. 30, 2023

(87) PCT Pub. No.: WO2022/230470
PCT Pub. Date: Nov. 3, 2022

(65) Prior Publication Data
US 2024/0216240 A1 Jul. 4, 2024

(30) Foreign Application Priority Data

Apr. 30, 2021 (JP) ................................. 2021-078157

(51) Int. Cl.
*A61K 8/42* (2006.01)
*A61K 8/891* (2006.01)
*A61Q 1/06* (2006.01)

(52) U.S. Cl.
CPC ................ *A61K 8/42* (2013.01); *A61K 8/891* (2013.01); *A61Q 1/06* (2013.01); *A61K 2800/592* (2013.01)

(58) Field of Classification Search
None
See application file for complete search history.

(56) References Cited

U.S. PATENT DOCUMENTS

2015/0164775 A1 6/2015 Julien et al.
2018/0263890 A1* 9/2018 Clavel ...................... A61Q 1/06

FOREIGN PATENT DOCUMENTS

| JP | H02180805 | A | | 7/1990 |
|---|---|---|---|---|
| JP | 2012149041 | A | | 8/2012 |
| JP | 2012214410 | A | | 11/2012 |
| JP | 2014177453 | A | * | 9/2014 |
| JP | 2014198705 | A | | 10/2014 |
| JP | 2015520212 | A | | 7/2015 |
| JP | 2017009452 | A | | 1/2017 |
| JP | 2015143195 | A | * | 5/2018 |
| JP | 2018203623 | A | | 12/2018 |
| JP | 2019099533 | A | | 6/2019 |
| JP | 2019119744 | A | | 7/2019 |
| JP | 7291034 | B | * | 3/2020 |
| JP | 2020033339 | A | | 3/2020 |
| WO | WO2009077709 | | * | 6/2009 |

OTHER PUBLICATIONS

International Bureau of WIPO, Preliminary Report on Patentability, Oct. 24, 2023, pp. 1-6.
Japan Patent Office, International Search Report for PCT/JP2022/013806, Jun. 7, 2022, pp. 1-2.
English abstract for JP2012214410A, Nov. 8, 2012.
English abstract for JP2018203623A, Dec. 27, 2018.
English abstract for JP2014177453A, Sep. 25, 2014.
English abstract for JP2020033339A, Mar. 5, 2020.
English abstract for JP2019119744A, Jul. 22, 2019.
English abstract for JP2012149041A, Aug. 9, 2012.
English abstract for JP2019099533A, Jun. 24, 2019.
English abstract for JP2014198705A, Oct. 23, 2014.
English abstract for JP2017009452A, Jan. 12, 2017.
English abstract for JPH02180805A, Jul. 13, 1990.
English machine translation for JPH02180805A, Jul. 13, 1990.
English Abstract for JP2015520212A, Jul. 16, 2015.

* cited by examiner

*Primary Examiner* — Danah Al-Awadi
(74) *Attorney, Agent, or Firm* — CAHN & SAMUELS, LLP

(57) ABSTRACT

The present invention is an oil-based liquid cosmetic containing: 60% by mass or more of polydimethylsiloxane (A); 0.01 to 1% by mass of N-acyl-L-glutamic acid dialkylamide (B); and 0.5 to 35% by mass of a compatibilizer (C) for compatibilizing the component (A) and the component (B). The oil-based liquid cosmetic preferably has a viscosity that is measured using a B-type rotational viscometer at 25° ° C. of 5 to 100,000 mPa·s.

9 Claims, No Drawings

OIL-BASED LIQUID COSMETIC

This application is a U.S. national stage application of PCT/JP2022/013806 filed on 24 Mar. 2022 and claims priority to Japanese patent document 2021-078157 filed on 30 Apr. 2021, the entireties of which are incorporated herein by reference.

TECHNICAL FIELD

The present invention relates to an oil-based liquid cosmetic excellent in spreadability, gloss, color transfer resistance, and stability.

BACKGROUND TECHNOLOGY

Oil-based liquid cosmetics, such as lip gloss, lipstick overcoat, liquid lipstick, are generally required to be excellent in gloss and emollient feeling after application while spreading with a light touch without stickiness upon application. It is also required that the cosmetics applied to the skin and lips are less likely to cause color transfer, which is also referred to as "secondary adhesion", that the cosmetic applied to the skin or lips is transferred to a contact site of a contacted body such as a garment or a cup. That is, the cosmetics are required to have a color transfer suppressing ability. Conventionally, formulating a silicone oil has been studied to solve these problems. For example, Patent Document 1 describes a technique of combining a phenyl silicone, a liquid multi-branched ester compound with a specific structure, and an oily gelling agent, and Patent Document 2 describes a technique of combining a silicone oil having a specific viscosity, a dimer dilinoleic acid derivative and a dextrin fatty acid ester. According to these techniques, it is possible to obtain an oil-based cosmetic having good gloss with less stickiness, but the cosmetic has not yet reached a sufficiently satisfactory level as to color transfer resistance. As used herein, "color transfer suppression ability" and "color transfer resistance" are used in the same meaning.

As an oily base for oil-based liquid cosmetics, silicone oils are known in addition to hydrocarbon oils and vegetable oils. For example, Patent Document 3 discloses an oil-based hair cosmetic containing dimethylpolysiloxane, which is a type of silicone oil, as a main component. On the other hand, N-acyl-L-glutamic acid dialkylamides represented by N-lauroyl-L-glutamic acid dibutylamide are known as oil gelling agents, and because they can gel many liquid oils transparently, there has been a wide consideration in recent years in the field of oil-based solid cosmetics having a stick form that require aesthetic properties. For example, Patent Document 4 describes a method of preparing a solid or semi-solid composition by formulating N-lauroyl-L-glutamic acid dibutyl amide in a skin care preparation containing methylphenylpolysiloxane, which is a type of polysiloxane, as a main base material. This reference indicates that the blending amount of N-lauroyl-L-glutamic acid dibutylamide is 0.1 to 10%, and that when the blending amount is less than 0.1%, it is less likely to exhibit the effect of the invention (see page 4, lower left column). Also disclosed in Patent Document 5 is a method for solidifying a branched higher alcohol by blending 1 to 30% by mass of a gelling agent such as dibutyl lauroyl glutamide (i.e., N-lauroyl-L-glutamic acid dibutylamide) (see paragraphs 0014 to 0015). Thus, most of examples on using oil gelling agents are for solidifying or semi-solidifying an oily base material, and there are few examples on formulating the oil gelling agents in the field of oil-based liquid cosmetics containing an oily base material in a liquid state. In particular, no example on formulating an N-acyl-L-glutamic acid dialkylamide in a liquid cosmetic containing dimethylpolysiloxane as the oily base material is known.

PRIOR ART DOCUMENT

Patent Document

Patent Document 1: Japanese Patent Laid-Open No. 2012-149041

Patent Document 2: Japanese Patent Laid-Open No. 2014-198705

Patent Document 3: Japanese Patent Laid-Open No. 2019-099533

Patent Document 4: Japanese Patent Laid-Open No. H02-180805

Patent Document 5: Japanese Patent Laid-Open No. 2017-009452

SUMMARY OF THE INVENTION

Problem to be Solved by the Invention

The present invention was completed based on such a background art, and an object thereof is to provide an oil-based liquid cosmetic excellent in spreadability, gloss, color transfer resistance, and stability.

Means Used to Solve the Problem

As a result of intensive studies to solve the above problem, the present inventors have found that, in oil-based liquid cosmetics, a combination of an incorporation of a small amount of N-acyl-L-glutamic acid dialkylamide to dimethylpolysiloxane used as a main base material and an incorporation of an oil agent having excellent solubility with both components is effective to improve properties of the oil-based liquid cosmetics. Thus, the present invention was completed.

Thus, according to the present invention, there is provided an oil-based liquid cosmetic containing containg 60% by mass or more of dimethylpolysiloxane (A), 0.01 to 1% by mass of N-acyl-L-glutamic acid dialkylamide (B) and 0.5 to 35% by mass of a compatibilizer (C) for compatibilizing the component (A) and the component (B).

Effect of the Invention

The oil-based cosmetic of the present invention is excellent in spreadability, gloss, color transfer resistance, and stability.

EMBODIMENT FOR CARRYING OUT OF THE INVENTION

In the present invention, the term "liquid" in the liquid cosmetic means that it is flowable at 25° C. The liquid preferably has a viscosity value of 5 to 100,000 mPa·s as measured by a B-type rotary viscometer at 25° C. More preferably, the viscosity value is 100 to 50,000 mPa, and furthermore preferably, the viscosity value is 1,000 to 20,000 Pa·s. Within such a range, liquid cosmetics with excellent gloss in addition to excellent feeling in use such as spreadability can be obtained. Being a liquid cosmetic has advantages of being easier to spread and having a smoother application surface compared to using a solid cosmetic, resulting in excellent gloss.

The oil-based liquid cosmetic of the present invention contains dimethylpolysiloxane (A) as a main base material and contains a small amount of N-acyl-L-glutamic acid dialkylamide (B) to adjust a viscosity thereof.

Preferably, dimethylpolysiloxane of the component (A) used in the present invention has a kinematic viscosity at 25° C. of 200 to 20,000 mm$^2$/s. More preferably, the kinematic viscosity is from 500 to 10,000 mm$^2$/s, in particular, from 800 to 8,000 mm$^2$/s. If the kinematic viscosity of dimethylpolysiloxane is too low, gloss and color transfer resistance tend to decrease. When it is too high, stickiness is likely to occur upon application, and it becomes difficult to spread the skin and lips.

Examples of commercially available dimethylpolysiloxane include KF-96 series manufactured by the Shin-Etsu Chemical Co., Ltd. and SH200 series manufactured by Dow Toray Co., Ltd. any of which is dimethicone that is a linear polymer having dimethylpolysiloxane structure with terminal portions blocked with a trimethylsiloxy group. These may be used alone, or in combination of two or more to adjust a viscosity appropriately.

A content of dimethylpolysiloxane of the component (A) in the oil-based cosmetic of the present invention is not particularly limited as long as it becomes a main base material. It is usually at least 60% by mass, preferably at least 70% by mass, more preferably at least 80% by mass. If the content of dimethylpolysiloxane is too low, color transfer resistance tends to decrease. It should be noted that in the present invention, "% by mass" is a proportion relative to the entire cosmetic unless otherwise noted.

N-acyl-L-glutamic acid dialkylamide of the component (B) used in the present invention is conventionally well known in the cosmetic field as an oily gelling agent, wherein one of the hydrogen atoms of the amino group of L-glutamic acid is substituted by an acyl group and the two carboxyl groups are converted to an alkylamide structure. The acyl group may include an unsaturated bond, or may be linear as well as branched. The acyl group usually has carbon atoms of 8 to 16, preferably 8 to 12. Examples of the acyl group include lauroyl group, 2-ethylhexanoyl group, and the like. Two alkyl groups forming the amide structure usually have carbon atoms of 1 to 18, preferably 2 to 6 respectively. Examples of which include ethyl, n-propyl, n-butyl, n-hexyl, and the like. The two alkyl groups may be the same or different. Preferred examples of N-acyl-L-glutamic acid dialkylamides include N-2-ethylhexanoyl-L-glutamic acid dibutylamide, N-lauroyl-L-glutamic acid dibutyl amide, and the like. N-acyl-L-glutamic acid dialkylamide may be used alone or in combination of two or more.

A content of the component (B) in the oi-based cosmetic of the present invention is 0.01 to 1% by mass, preferably 0.03 to0.5% by mass, more preferably 0.05 to 0.1% by mass. If the content is too large, smoothness of application is lacked and gloss after application also decreases. When content is excessively small, sedimentation of powders tends to occur in a formulation containing powders.

N-acyl-L-glutamic acid dialkylamide of the component (B) may be commercially available product. Examples of the commercial product of N-lauroyl-L-glutamic acid dibutyl amide include Geranization Agent GP-1 manufactured by manufactured by Ajinomoto Co., Inc. Examples of the commercial product of N-2-ethylhexanoyl-L-glutamic acid dibutylamide include Gelanization Agent EB-21 manufactured by Ajinomoto Co., Inc.

The component (C) in the oil-based cosmetic of the present invention is a compatibilizer for compatibilizing the component (A) and the component (B). Since the component (B) used in the present invention has a low solubility in the component (A), even when heated at 150° C., it is difficult to make a cosmetic having a uniform viscosity with only the components (A) and (B). The component (C) is an oil being liquid at 25° C. with a higher solubility of the component (B) than the component (A), which can form a homogeneous liquid mixture without causing phase separation when preparing an equivalent mixture with the component (A). Preferably, the component (C) is an oil capable of forming a uniform liquid mixture at room temperature (25° C.) when preparing a mixture in which a ratio by mass of components (A), (B), and (C), that is, [(A)/(B)/(C)] is 94.9/0.1/3. More preferably, the component (C) is an oil capable of forming a uniform liquid mixture at room temperature (25° C.) when preparing a mixture with a ratio by mass of components (A), (B), and (C) represented by the formula [(A)/(B)/(C)] of 96.9/0.1/3. By using the component (C), a dissolution temperature of the component (B) in a manufacturing process of the cosmetic can be set low, and a moderately uniform thickened liquid mixture can be obtained.

The component (C) is not particularly limited as long as it satisfies the above requirements, and examples thereof include a hydrocarbon oil, a higher fatty acid, a higher alcohol, and an ester oil. In addition, a cyclic silicone or a modified silicone oil which is more compatible with the hydrocarbon oil than the component (A) can be exemplified.

Examples of the hydrocarbon oil that is liquid at 25° C. includes hydrocarbons having carbon atoms of 12 to 40 that may be saturated or unsaturated, and linear or branched, and more specifically, include isododecane, isohexadecane, isoparaffin, polybutene, polyisobutylene, liquid paraffin, alpha-olefin oligomer, squalane, and petrolatum.

Examples of the higher fatty acid that is liquid at 25° C. include fatty acids having 12 to 36 carbon atoms that may saturated or unsaturated, linear or branched, and more specifically, include isostearic acid, hexyl decanoic acid, oleic acid, and linoleic acid.

Examples of the higher alcohol that is liquid at 25° C. include higher alcohols having carbon atoms of 12 to 36 that may be saturated or unsaturated, and linear or branched, and more specifically, include isostearyl alcohol, hexyldecanol, and octyldodecanol.

Examples of the ester oil that is liquid at 25° C. include esters composed of fatty acids having carbon atoms of 3 to 24 and alcohols having carbon atoms of 3 to 24, esters composed of fatty acids having carbon atoms of 8 to 24 and polyhydric alcohols, and esters composed of carbonic acid and alcohols having carbon atoms of 8 to 24. Specific examples of the ester composed of fatty acids having carbon atoms of 3 to 24 and alcohols having carbon atoms of 3 to 24 include isononyl isononanoate, isodecyl isononanoate, isotridecyl isononanoate, ethylhexyl palmitate, cetyl ethylhexanoate, isopropyl myristate, isopropyl palmitate, octyldodecyl myristate, diisostearyl malate, isodecyl neopentanoate, hexyl laurate, 2-hexyldecyl laurate, isotridecyl myristate, isocetyl palmitate, isodecyl palmitate, isostearyl palmitate, 2-octyldecyl palmitate, isopropyl stearate, 2-octyldodecyl stearate, isostearyl isostearate, 2-octyldodecyl erucate, and jojoba oil. Examples of the ester composed of fatty acids having carbon atoms of 8 to 24 and polyhydric alcohols include caprylic/capric triglyceride, triethylhexanoin, diglyceryl triisostearate, decaglyceryl decaisostearate, diglyceryl tetraisostearate, neopentyl glycol dioctanoate, olive oil, castor oil, mink oil, macadamia nut oil. Examples of the ester composed of carbonic acid and alcohols having carbon atoms of 8 to 24 include dicaprylyl carbonate.

Examples of silicone oils other than the component (A) include cyclic silicones, phenyl-modified silicones, methyl-trimethicone, and caprylyltrimethicone.

Among these, from the viewpoint of uniform dissolution of N-acyl-L-glutamic acid dialkylamide of the component (B) and good compatibility with the component (A), ester oils being liquid at 25° C. and phenyl-modified silicones are preferably used. In particular, an ester oil having a branched chain derived from a branched higher fatty acid or a branched higher alcohol such as isononyl isononanoate, isotridecyl isononanoate, triethylhexanoin and 2-ethylhexyl palmitate, and methylphenylpolysiloxane are preferably used.

A content of the compatibilizer (C) is 0.5% to 35% by mass, preferably 1% to 15% by mass, more preferably 3% to 10% by mass. If the content of the compatibilizer is too low, it becomes difficult to dissolve the component (B) in the component (A), resulting in poor uniformity of the formulation. Conversely, if too high, color transfer resistance is reduced.

The oil-based liquid cosmetic of the present invention may contain components used in conventional cosmetics, such as powders, dyes, solid oils, oily gelling agents other than the component (B), oil-soluble resins, polyhydric alcohols, lower alcohols, ultraviolet absorbers, ultraviolet scattering agents, humectants, perfumes, antioxidants, preservatives, antifoaming agents, various extracts, and the like, within a range that does not inherently impair the effects of the present invention.

The oil-based liquid cosmetic of the present invention can be prepared according to conventional methods. For example, after whole raw materials are mixed and heated to obtain a uniform melt, the melted mixture is poured into various containers and cooled or allowed to cool to obtain an oil-based liquid cosmetic.

The oil-based liquid cosmetic of the present invention can be used for a lipstick, a lip gloss, a lipstick overcoat, a lipstick base, a lip essence, and the like. In particular, it is suitable for a lipstick and a lip gloss or a lipstick overcoat because it gives a cosmetic film that is excellent in gloss, color transfer resistance, color retention and gloss persistence.

EXAMPLE

Hereinafter, the invention will be described further with reference to Example and Comparative Examples, but the present invention is not limited by these Examples. A compounding amount in formulations in the following description is "% by mass" relative to the total amount unless otherwise noted.

The method for evaluating the oil-based liquid cosmetics in the following Examples and Comparative Examples is as follows.

Evaluation item I: Spreadability
Evaluation item II: Gloss
Evaluation item III: Color transfer resistance (1)
Evaluation item IV: Color transfer resistance (2)
Evaluation item V: Uniformity of formulation
Evaluation item VI: Stability For each of the evaluation items I to III, 10 evaluators applied a sample to their lips and evaluated sensorily in 5 stages based on the following scoring standard (score).

Evaluation results were determined according to the following evaluation criteria based on an average value of scores by ten evaluators.

Score

5: Very good.

4: Good

3: Ordinary

2: Poor

1: very poor.

Evaluation Criteria

S: Average value of scores is 4.0 or more.

A: Average value of scores is 3.5 or more and less than 4.0.

B: Average value of scores is 2.5 or more and less than 3.5.

C: Average value of scores is less than 2.5.

<Evaluation Item IV: Color Ttransfer Resistance (2)>

As for a lipstick overcoat, color transfer resistance (2) described as evaluation item IV was evaluated. Specifically, after a lipstick is applied to an artificial skin (trade name: BIOSKIN PLATE which is available from Beaulax Co., Ltd.), and subsequently applying an oil-based liquid cosmetic for evaluation at a ratio of about 2 mg/cm² thereon, a tissue paper was placed and lightly suppressed to observe a degree of color transfer of the lipstick to the tissue paper. Evaluation criteria are as follows.

Evaluation Criteria

S: No apparent color transfer is observed even after the third pressing.

A: A slight color transfer is observed at the second pressing, and an apparent color transfer is observed at the third pressing.

B: A slight color transfer is observed at the first pressing, and an apparent color transfer is observed at the second pressing.

C: An apparent color transfer is observed at the first pressing,

<Evaluation Item V: Uniformity of Formulation>

A formulation was lightly spread on an artificial skin (trade name: BIOSKIN PLATE which is available from Beaulax Co., Ltd.) with a spatula to evaluate uniformity of formulation. When the entire formulation was a uniform viscous liquid, it was determined as S, and when the formulation contained a gel-like portion and a liquid portion, it was determined as C.

<Evaluation Item VI: Stability>

As for a lips gloss, stability described as evaluation item VI was evaluated. A sample placed in a glass bottle was stored in a constant temperature bath at 60° C., and a degree of sedimentation of coloring materials and pearlescent agents was observed after one week elapsed. It was determined as S when no sedimentation was observed, A when slight sedimentation was observed, B when clear sedimentation was observed, and C when complete sedimentation was observed.

7

Examples 1 to 5 and Comparative Examples 1 to 4

<Lipstick Overcoat>

A lipstick overcoat having the formulation shown in Table 1 was prepared according to the following manufacturing procedure and evaluated for spreadability, uniformity of formulation, gloss, and color transfer resistance (2) according to the method described above. The results are shown in Table 1.

Manufacturing Procedure (1) The ingredients 1 to 14 shown in Table 1 were heated to about 135° C. and uniformly mixed.
(2) The mixture prepared in the above (1) was filled into a lip gloss container with a cap having an applicator and allowed to cool to obtain a lipstick overcoat.

8

As seen from the results shown in Table 1, the lipstick overcoat of the present invention was excellent in spreadability, gloss, color transfer resistance, and uniformity of formulation (refer to Examples 1 to 5). On the other hand, the lipstick overcoat of Comparative Example 1 in which polybutene, that is widely used in conventional oil-based liquid cosmetics an example of which is described in Patent Document 2, was used, was significantly inferior in color transfer resistance. In Comparative Examples 2 and 4, which contained a large amount of phenyl-modified silicone instead of the component (A), not only was uniformity of formulation impaired, but also color transfer resistance was poor. The lipstick overcoat of Comparative Example 3 having a blending amount of the component (A) of less than 60% by mass was greatly inferior in color transfer resistance.

TABLE 1

| | | | Example | | | | | Comparative Example | | | |
|---|---|---|---|---|---|---|---|---|---|---|---|
| | | Ingredient | 1 | 2 | 3 | 4 | 5 | 1 | 2 | 3 | 4 |
| 1 | A | Dimethylpolysiloxan(3,000 mm$^2$/s) (※1) | 94.93 | | | | | | | | |
| 2 | A | Dimethylpolysiloxan(1,000 mm$^2$/s) (※2) | | 94.90 | | | | 10.00 | | | |
| 3 | A | Dimethylpolysiloxan(5,000 mm$^2$/s) (※3) | | | | 89.93 | 64.93 | | | 54.93 | 59.93 |
| 4 | A | Dimethylpolysiloxan(100,000 mm$^2$/s) (※4) | | | 30.00 | | | | | | |
| 5 | A | Dimethylpolysiloxan(100 mm$^2$/s) (※5) | | | 64.95 | | | | | | |
| 6 | | Polybutene(※6) | | | | | | 40.00 | | | |
| 7 | B | N-lauroyl-L-glutamic acid dibutylamide (※7) | 0.04 | 0.10 | | 0.04 | 0.04 | | 0.04 | 0.04 | 0.04 |
| 8 | B | N-2-ethylhexanoyl-L-glutamic acid dibutylamide (※8) | 0.03 | | 0.05 | 0.03 | 0.03 | | 0.03 | 0.03 | 0.03 |
| 9 | | Dextrin palmitate(※9) | | | | | | 5.00 | | | |
| 10 | C | Isononyl isononanoate(※10) | 5.00 | 5.00 | 5.00 | 10.00 | | 15.00 | 5.00 | 45.00 | |
| 11 | C | Diphenylsiloxyphenyl trimethicone(15 mm$^2$/s) (※11) | | | | | 35.00 | | | | |
| 12 | C | Diphenylsiloxydimethicone(5,000 mm$^2$/s) (※12) | | | | | | 10.00 | 94.93 | | 40.00 |
| 13 | | Dimer dilinoleic acid derivative(※13) | | | | | | 5.00 | | | |
| 14 | | Diglyceryl triisostearate(※14) | | | | | | 15.00 | | | |
| Evaluation | | Spreadability | S | S | S | S | S | A | C | S | A |
| | | Gloss | A | S | S | S | S | B | S | B | S |
| | | Clor transfer resistance (2) | A | A | S | S | A | C | B | C | B |
| | | Uniformity of formulatioon | S | A | S | S | S | S | C | S | C |

※1 Trade name SILICONE KF-96 3,000CS (Shin-Etsu Chemical Co., Ltd.)
※2 Trade name SILICONE KF-96 1,000CS (Shin-Etsu Chemical Co., Ltd.)
※3 Trade name SILICONE KF-96 5,000CS (Shin-Etsu Chemical Co., Ltd.)
※4 Trade name SILICONE KF-96H 100,000CS (Shin-Etsu Chemical Co., Ltd.)
※5 Trade name SILICONE KF-96 100CS (Shin-Etsu Chemical Co., Ltd.)
※6 Trade name PURIFIED POLYBUTENE HV-100F (Japan Natural Products Co., Ltd.)
※7 Trade name Gelanization Agent GP-1 (Ajinomoto Co., Inc.)
※8 Trade name Gelanization Agent EB-21 (Ajinomoto Co., Inc.)
※9 Trade name RHEOPEARL KS2 (Chiba Flour Milling Co., Ltd.)
※10 Trade name SALACOS 99 (The Nissin Oillio Group Co., Ltd.)
※11 Trade name KF-56A (Shin-Etsu Chemical Co., Ltd.)
※12 Trade name KF-54HV (Shin-Etsu Chemical Co., Ltd.)
※13 Trade name Plandool-H (Nippon Fine Chemical Co., Ltd.)
※14 Trade name COSMOL 43V (The Nissin Oillio Group Co., Ltd.)

Examples 6, 7 and Comparative Examples 5 to 9

<Lip Gloss>

A lip gloss having the formulation shown in Table 2 was prepared according to the above manufacturing procedure and evaluated for spreadability, gloss, color transfer resistance (1), and uniformity of formulation according to the method described above. The results are shown in Table 2.

TABLE 2

| | | Ingredient | Example 6 | Example 7 | Comparative Example 5 | Comparative Example 6 | Comparative Example 7 | Comparative Example 8 | Comparative Example 9 |
|---|---|---|---|---|---|---|---|---|---|
| 1 | A | Dimethylpolysiloxan(5,000 mm²/s) (※3) | 94.42 | 94.02 | | 99.42 | 94.37 | 93.52 | 93.52 |
| 2 | A | Dimethylpolysiloxan(100,000 mm²/s) (※4) | | | 30.00 | | | | |
| 3 | A | Dimethylpolysiloxan(100 mm²/s) (※5) | | | 64.52 | | | | |
| 4 | B | N-lauroyl-L-glutamic acid dibutylamide (※7) | 0.10 | 0.50 | | 0.10 | | | |
| 5 | | Hydroxystearic acid(※15) | | | | | 0.15 | | |
| 6 | | Inulin stearate(※16) | | | | | | 1.00 | |
| 8 | | Polyamide-8(※17) | | | | | | | 1.00 |
| 9 | C | Isotridecyl isononanoate(※18) | 5.00 | 5.00 | 5.00 | | 5.00 | 5.00 | 5.00 |
| 10 | | Hydrophobic surface-treated titanium oxide | 0.10 | 0.10 | 0.10 | 0.10 | 0.10 | 0.10 | 0.10 |
| 11 | | Red No. 202 | 0.01 | 0.01 | 0.01 | 0.01 | 0.01 | 0.01 | 0.01 |
| 12 | | Aluminum lake of Yellow No. 4 | 0.07 | 0.07 | 0.07 | 0.07 | 0.07 | 0.07 | 0.07 |
| 13 | | Titanium oxide-coated synthetic phlogopite | 0.30 | 0.30 | 0.30 | 0.30 | 0.30 | 0.30 | 0.30 |
| Evaluation | | Spreadability | S | A | S | S | C | C | C |
| | | Gloss | S | S | S | S | S | S | S |
| | | Color transfer resistance (1) | S | S | S | S | S | S | S |
| | | Uniformity of formulatioon | S | S | S | C | C | C | C |
| | | Stability | S | S | C | A | A | C | C |

※15 Trade name HYDROXYSTEARIC ACID (NOFCorporation)
※16 Trade name RHEOPEARL ISK (Chiba Flour Milling Co., Ltd.)
※17 Trade name SP OLEOCRAFT LP-20 (Croda Japan K.K.)
※18 Trade name SALACOS 913 (The Nissin Oillio Group Co., Ltd.)

As shown in Table 2, the lip gloss of the present invention was excellent in spreadability, gloss, color transfer resistance, uniformity of formulation, and stability (refer to Examples 6 and 7), whereas the lip gloss of Comparative Example 5 not containing the component (B) resulted in poor stability, and the lip gloss of Comparative Example 6 not containing the component (C) did not completely dissolve the component (B), resulting in poor uniformity of formulation. In addition, any lip glosses of Comparative Examples 7 to 9 containing an oily gelling agent other than the component (B) wase remarkably inferior in spreadability.

Example 8

<Liquid Lipstick>

A liquid lipstick having the formulation shown in Table 3 was prepared according to the above manufacturing procedure and evaluated for spreadability, gloss, color transfer resistance (1), uniformity of formulation, and stability according to the method described above. The results are shown in Table 3.

Manufacturing Procedure (1) The components 1 to 9 shown in Table 3 were heated to about 130° C. and uniformly mixed.

(2) After cooling the mixture prepared in the above (1), it was filled into a lip gloss container with a cap having an applicator to obtain a liquid lipstick.

TABLE 3

| | | Ingredient | Example 8 |
|---|---|---|---|
| 1 | A | Dimethylpolysiloxan(3,000 mm²/s) (※1) | 92.93 |
| 2 | B | N-lauroyl-L-glutamic acid dibutylamide (※7) | 0.04 |
| 3 | B | N-2-ethylhexanoyl-L-glutamic acid dibutylamide (※8) | 0.03 |

TABLE 3-continued

| | | Ingredient | Example 8 |
|---|---|---|---|
| 4 | C | Isononyl isononanoate (※18) | 5.00 |
| 5 | | Red No. 202 | 0.50 |
| 6 | | Aluminum lake of Yellow No. 4 | 0.30 |
| 7 | | Aluminum lake of Blue No. 1 | 0.20 |
| 8 | | (Titanium oxide and silica)-coated calcium aluminum borosilicate | 0.50 |
| 9 | | (titaniumu oxide and silica)-coated calcium aluminum borosilicate | 0.50 |
| Evaluatin | | Spreadability | S |
| | | Gloss | S |
| | | Color transfer resistance (1) | S |
| | | Uniformity of formulatioon | S |
| | | Stability | S |

※19 Trade name METASHINE MT1080SS1 (Nioppon Sheet Glass Company Ltd.)
※20 Trade name METASHINE MT1080RGS1 (Nippon Sheet Glass Company Ltd.)

As seen from the results shown in Table 3, the liquid lipstick of Example 8 was excellent in spreadability, gloss, color transfer resistance, uniformity of formulation and stability.

INDUSTRIAL APPLICABILITY

According to the present invention, there is provided an oil-based liquid cosmetic that is excellent in spreadability, gloss, color transfer resistance, and stability.

What is claimed is:

1. An oil-based liquid cosmetic comprising:
60% by mass or more of dimethylpolysiloxane (A),
0.01 to 1% by mass of N-acyl-L-glutamic acid dialkyl-amide (B), and 3 to 35% by mass of a compatibilizer (C) for compatibilizing the component (A) and the component (B), wherein the compatibilizer comprises an ester oil that is liquid at 25° C. or a phenyl-modified silicone that is liquid at 25° C.

2. The oil-based liquid cosmetic according to claim 1, wherein the N-acyl-L-glutamic acid dialkylamide has an acyl group having 8 to 18 carbon atoms and the alkyl group having 1 to 8 carbon atoms.

3. The oil-based liquid cosmetic according to claim 1, wherein the dimethylpolysiloxane has a kinematic viscosity of 200 to 20,000 mm²/s at 25° C.

4. The oil-based liquid cosmetic according to claim 1 having a viscosity of 5 to 100,000 mPas as measured by a B-type rotary viscometer at 25° C.

5. The oil-based liquid cosmetic according to claim 1, wherein a content of the component (B) is 0.03 to 0.5% by mass.

6. The oil-based liquid cosmetic according to claim 1, which is a liquid lipstick, a lip gloss, a lipstick overcoat, a lipstick base or a lip essence.

7. An oil-based liquid cosmetic according to claim 1, wherein the compatibilizer comprises an ester oil that is liquid at 25° C.

8. The oil-based liquid cosmetic according to claim 7, wherein the ester oil comprises isononyl isononanoate, isodecyl isononanoate, isotridecyl isononanoate, ethylhexyl palmitate, cetyl ethylhexanoate, isopropyl myristate, isopropyl palmitate, octyldodecyl myristate, diisostearyl malate, isodecyl neopentanoate, hexyl laurate, 2-hexyldecyl laurate, isotridecyl myristate, isocetyl palmitate, isodecyl palmitate, isostearyl palmitate, 2-octyldecyl palmitate, isopropyl stearate, 2-octyldodecyl stearate, isostearyl isostearate, 2-octyldodecyl erucate, caprylic/capric triglyceride, triethylhexanoin, diglyceryl triisostearate, decaglyceryl decaisostearate, diglyceryl tetraisostearate, neopentyl glycol dioctanoate, or dicaprylyl carbonate.

9. An oil-based liquid cosmetic comprising:

60% by mass or more of dimethylpolysiloxane;

0.01 to 1% by mass of N-acyl-L-glutamic acid dialkylamide; and 3 to 35% by mass of an ester oil that is liquid at 25° C. or a phenyl-modified silicone that is liquid at 25° C., wherein the cosmetic is a liquid.

* * * * *